United States Patent
McGlothen

(12)
(10) Patent No.: US 6,536,436 B1
(45) Date of Patent: *Mar. 25, 2003

(54) STRAP FOR NASAL CANNULA

(76) Inventor: Roberta McGlothen, 13930 2nd Ave. West, Orofino, ID (US) 83544

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/427,865

(22) Filed: Oct. 26, 1999

(51) Int. Cl.$^7$ ............................................. A61M 15/08
(52) U.S. Cl. ........................... 128/207.18; 128/200.24; 128/200.18
(58) Field of Search .................. 128/200.24, 204.18, 128/207.11, 207.17, 207.18, DIG. 26; 607/139–141

(56) References Cited

U.S. PATENT DOCUMENTS

| | | | |
|---|---|---|---|
| 2,259,817 A | | 10/1941 | Hawkins |
| 2,292,568 A | | 8/1942 | Kanter et al. |
| 2,353,643 A | | 7/1944 | Bulbulian |
| 4,018,221 A | | 4/1977 | Rennie |
| 4,106,505 A | * | 8/1978 | Salter et al. ............ 128/207.18 |
| 4,278,082 A | | 7/1981 | Blackmer .............. 128/207.18 |
| 4,331,143 A | | 5/1982 | Foster ................... 128/207.17 |
| 4,406,283 A | | 9/1983 | Bir ......................... 128/207.18 |
| 4,480,639 A | | 11/1984 | Peterson et al. ....... 128/207.18 |
| 4,569,348 A | | 2/1986 | Hasslinger .................. 604/179 |
| 4,739,757 A | | 4/1988 | Edwards ................ 128/207.18 |
| 4,836,200 A | | 6/1989 | Clark ..................... 128/207.18 |
| 5,117,818 A | | 6/1992 | Palfy ..................... 128/204.11 |
| 5,284,469 A | | 2/1994 | Jasen et al. .................. 602/17 |
| 5,342,317 A | | 8/1994 | Claywell .................... 604/179 |
| 5,345,931 A | | 9/1994 | Battaglia, Jr. ......... 128/207.17 |
| 5,490,504 A | | 2/1996 | Vrona et al. ........... 128/207.17 |
| 5,520,656 A | | 5/1996 | Byrd ......................... 604/180 |
| 5,611,810 A | * | 3/1997 | Arnold et al. ............... 606/185 |
| 5,643,308 A | * | 7/1997 | Markman .................... 606/187 |
| 5,645,058 A | * | 7/1997 | Odom .................. 128/DIG. 26 |
| 5,653,228 A | | 8/1997 | Byrd ...................... 128/207.11 |
| 5,674,202 A | * | 10/1997 | Atallah ................ 128/DIG. 26 |
| 5,687,715 A | | 11/1997 | Landis et al. .......... 128/207.18 |
| 5,704,916 A | | 1/1998 | Byrd .......................... 604/179 |
| 5,879,335 A | | 3/1999 | Martinez et al. ............. 604/179 |
| 5,931,794 A | * | 8/1999 | Pitesky ....................... 600/556 |
| 6,083,196 A | * | 7/2000 | Trautman et al. ............. 604/46 |

* cited by examiner

Primary Examiner—Glenn K. Dawson
(74) Attorney, Agent, or Firm—Pedersen & Co., PLLC; Ken J. Pedersen; Barbara S. Pedersen

(57) ABSTRACT

The present invention is a convenient and inexpensive strap for securely and comfortably holding a nasal cannula to the head of a wearer. Typically the strap is made of a soft cloth or foam fabric, about ⅛–¾ inch wide and 6–16 inches long. Preferably the strap has strips of both hook and loop fasteners about ½–3 inches long at each end on one same side of the cloth. To use the strap, one end of it is looped around one of the oxygen tubes and secured to itself. The strap extends behind the ears of the wearer, and rests on the back of the head or the nape of the neck of the wearer. Then, the other end of the strap is looped around the other oxygen tube and secured to itself. The tension in the strap may be adjusted to pull the tubes in slightly towards the middle of the back of the head or neck, which may also pull the tubes off of the back of the ears. This way, the cannula may be conveniently, securely, and comfortably attached to the head of the wearer. This securement reduces the tendency of the tubes to move relative to the users skin and ears, and therefore, without lifting the tubes up off the ears, it may reduce chafing of the skin and ears. Also, the invented strap requires no additional cap, harness, or head-encircling strap, and so it is not psychologically or physically burdensome.

3 Claims, 5 Drawing Sheets

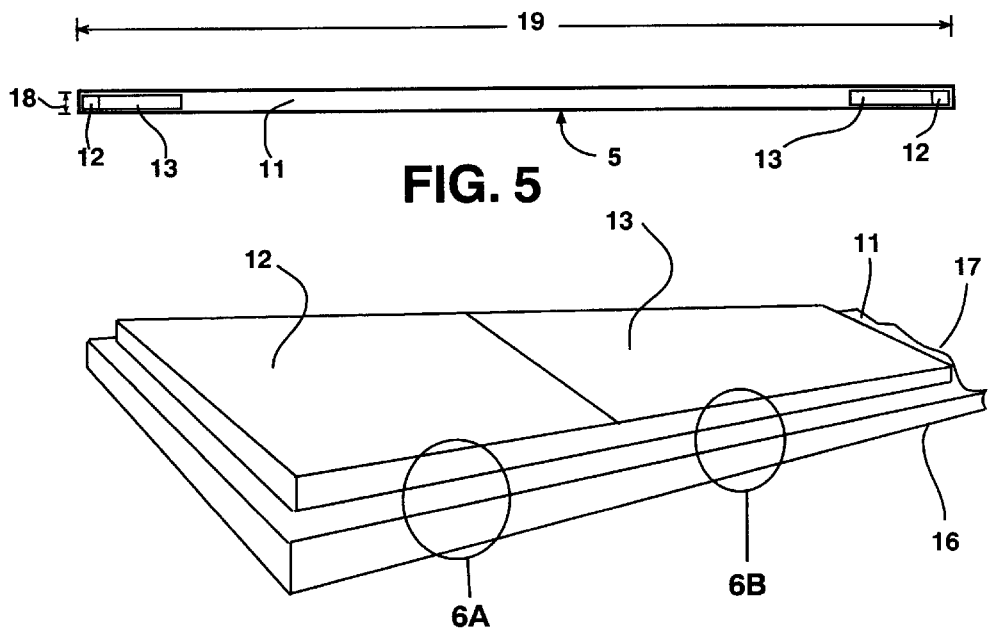
FIG. 5
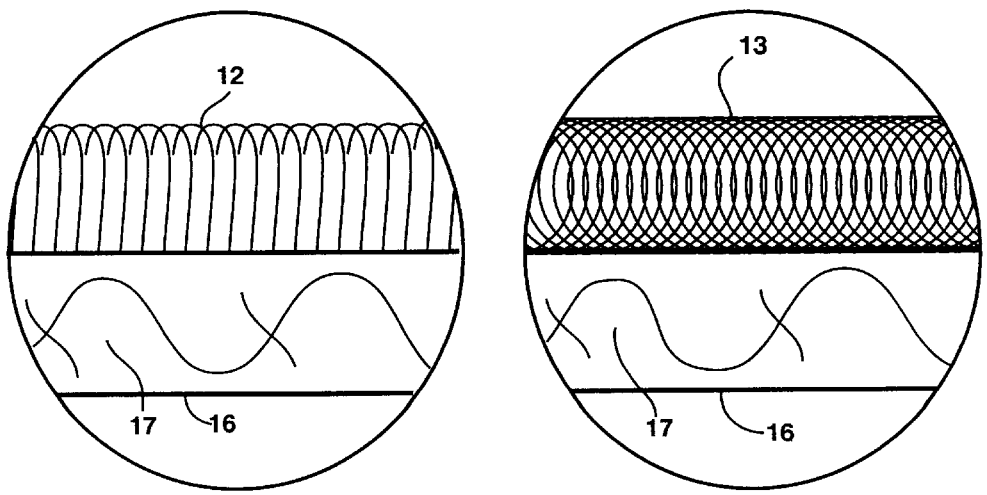
FIG. 6
FIG. 6A
FIG. 6B

STRAP FOR NASAL CANNULA

BACKGROUND OF THE INVENTION

1. Field of the Invention

This invention relates generally to nasal cannula devices for assisting breathing in humans. More specifically, this invention relates to a convenient and inexpensive strap for securely but comfortably holding the nasal cannula to the head of the wearer.

2. Related Art

Many people wear nasal cannula to assist them in breathing. Typically, pure oxygen or air enriched in oxygen is provided under slight positive pressure through plastic tubes to the nostrils of the wearer of the cannula. This way, more oxygen is provided to the lungs of the wearer.

The nasal cannula, however, must be securely held in place under the nostrils of the wearer. This securement of the cannula often causes discomfort for the wearer. Typically, chafing of the oxygen tubes on the cheeks and over the ears of the wearer are experienced when prior art securement techniques are utilized. Also, the cannula often may be easily dislodged during sleeping, reducing its effectiveness Several devices have already been invented to address this discomfort and security problem.

For example, U.S. Pat. No. 2,259,817 (Hawkins), U.S. Pat. No. 2,292,568 (Kanter et al.), and U.S. Pat. No. 4,333,143 (Foster) disclose straps which encircle the head to hold a cannula in place. Also, U.S. Pat. No. 5,117,818 (Palfy) and U.S. Pat. No. 5,653,228 (Byrd '228) disclose straps which support additional, separate securing devices for holding the cannula next to the face. Finally, U.S. Pat. No. 5,704,916 (Byrd '916) discloses a strap which extends over the top of the head and holds the cannula up off the ears with clips at the end of the strap.

Still, there is a need for a convenient and inexpensive securement means for holding the nasal cannula securely but comfortably to the head of the wearer, but with less structure than prior art devices. This invention addresses that need.

This invention is a simple, and inexpensive strap for stabilizing a nasal cannula on a wearer. Preferably, the strap has both hook and loop fasteners at each end. The strap is attached directly to both of the oxygen tubes behind the ears, and rests on the back of the head or nape of the neck of the wearer. This way, the cannula may be conveniently and securely attached to the head of the wearer.

SUMMARY OF THE INVENTION

The present invention is a convenient and inexpensive strap for securely and comfortably holding a nasal cannula to the head of a wearer. Typically the strap is made of a soft cloth or foam fabric, about ⅛–¾ inch wide and 6–16 inches long. Preferably, the strap has strips of both hook and loop fasteners about ⅛–2 inches long at each end on one same side of the cloth. To use the strap, one end of it is looped and secured to itself around one of the oxygen tubes, at a position on the oxygen tube generally between the ear and the shoulder. The strap extends behind the ears of the wearer, and rests on back of the head or the nape of the neck of the wearer. Then, the other end of the strap is looped around the other oxygen tube and secured to itself, in a mirror-image position between the other ear and other shoulder of the patient.

When in use, the invented strap is preferably entirely below the patient's ears and is substantially behind the patient's ears. The strap preferably does not encircle any part of the patient's body, except that the strap tends to curve around the back of the neck, that is, about ⅓–½ way around the neck. The tension in the strap may be adjusted to pull the tubes in slightly towards the middle of the back of the head or neck. While preferably holding the cannula off of the back of the ears and holding the cannula from falling off the ears, the invented strap preferably still allows some movement of the cannula, relative to the user's ears, the neck, and the strap itself. This way, the cannula may be conveniently and securely attached to the head of the wearer, while giving the user both a more secure and comfortable feeling.

BRIEF DESCRIPTION OF THE DRAWINGS

FIG. 5 is a schematic outside surface view of an embodiment of the invention.

FIG. 6 is a schematic partial perspective view, including two magnified detail views, FIGS. 6A and 6B, of one end of an embodiment of the strap of the invention.

DESCRIPTION OF THE PREFERRED EMBODIMENTS

Referring to the Figures, there is depicted one, but not the only, embodiment of the present invention. As illustrated in the Figures, the invented strap 5 is a simple, efficient system for increasing security and comfort for oxygen cannula wearers. The invented strap need only be connected to the cannula tubes, and need not be attached to the nosepiece of the cannula. The invented strap helps insure that the cannula tubes will not fall off or become pulled off the ears. The invented strap increases comfort because it reduces/eliminates the chaffing of the cannula tubes on the ears and because it is inherently more comfortable to wear a cannula system if the cannula tubes are not shifting in position with every slight movement of the wearer.

FIGS. 1–4 illustrate the preferred design and use of the invented strap 5. The preferred embodiment attached directly to the cannula tubes, and includes no band or attachment around any portion of the user's body, no strap over the user's head, and no attachment to any other clothing or apparatus besides the left and right cannula tubes.

Figure 1:
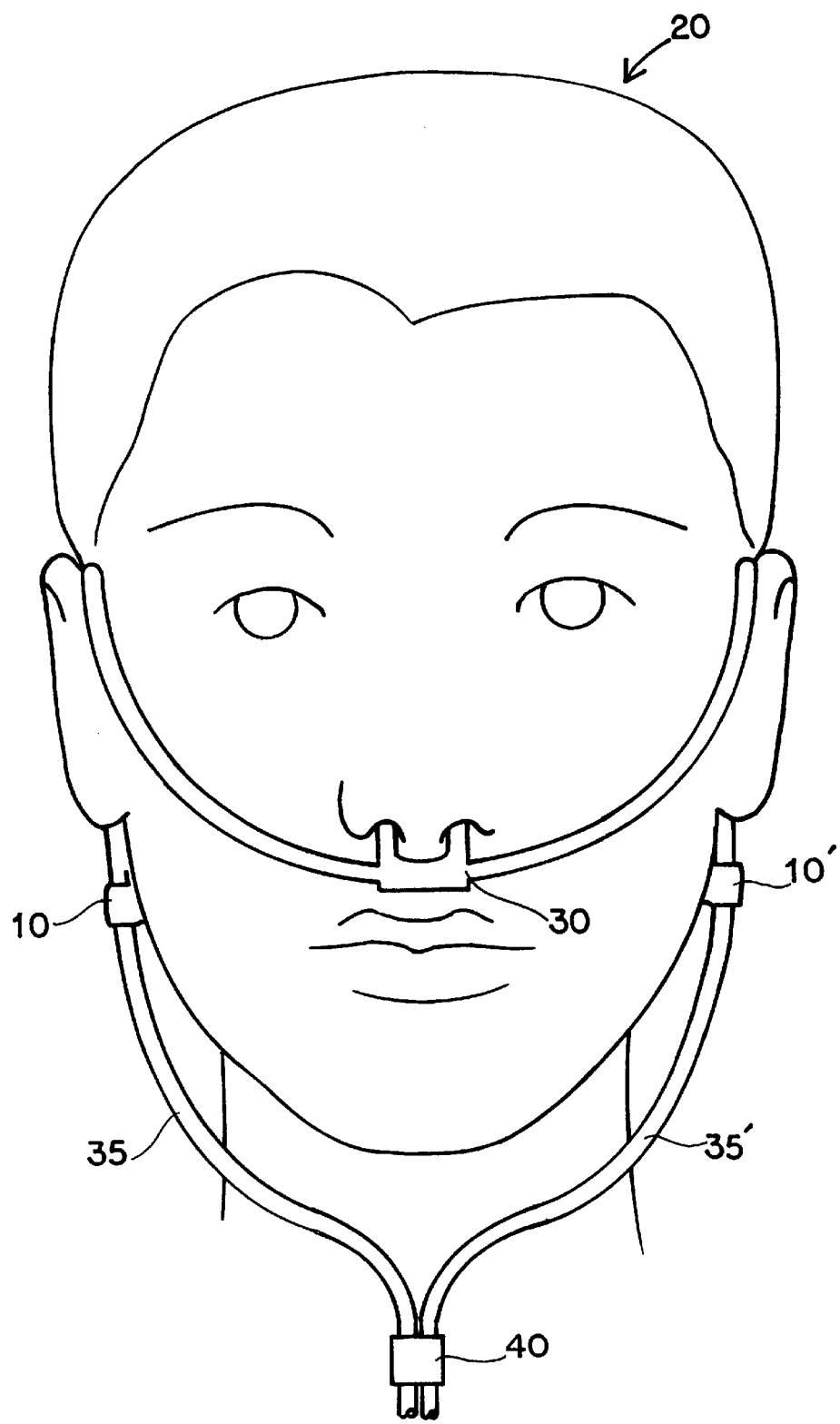
FIG. 1 is a front view of a user wearing an embodiment of the invention.

On front view FIG. 1, strap loops 10 and 10' of the invention may be seen beneath the ears on each side of and behind the wearer's 20 head. Nasal cannula 30 has hollow, plastic tubes 35 and 35' which extend from both of the wearer's nostrils, up over both cheeks beneath the eyes, up over both ears, and down over the top of both shoulders to be joined by clip 40 at the front of the chest. Then, the cannula tubes 35 and 35' extend to an oxygen source (not shown).

Figure 2:
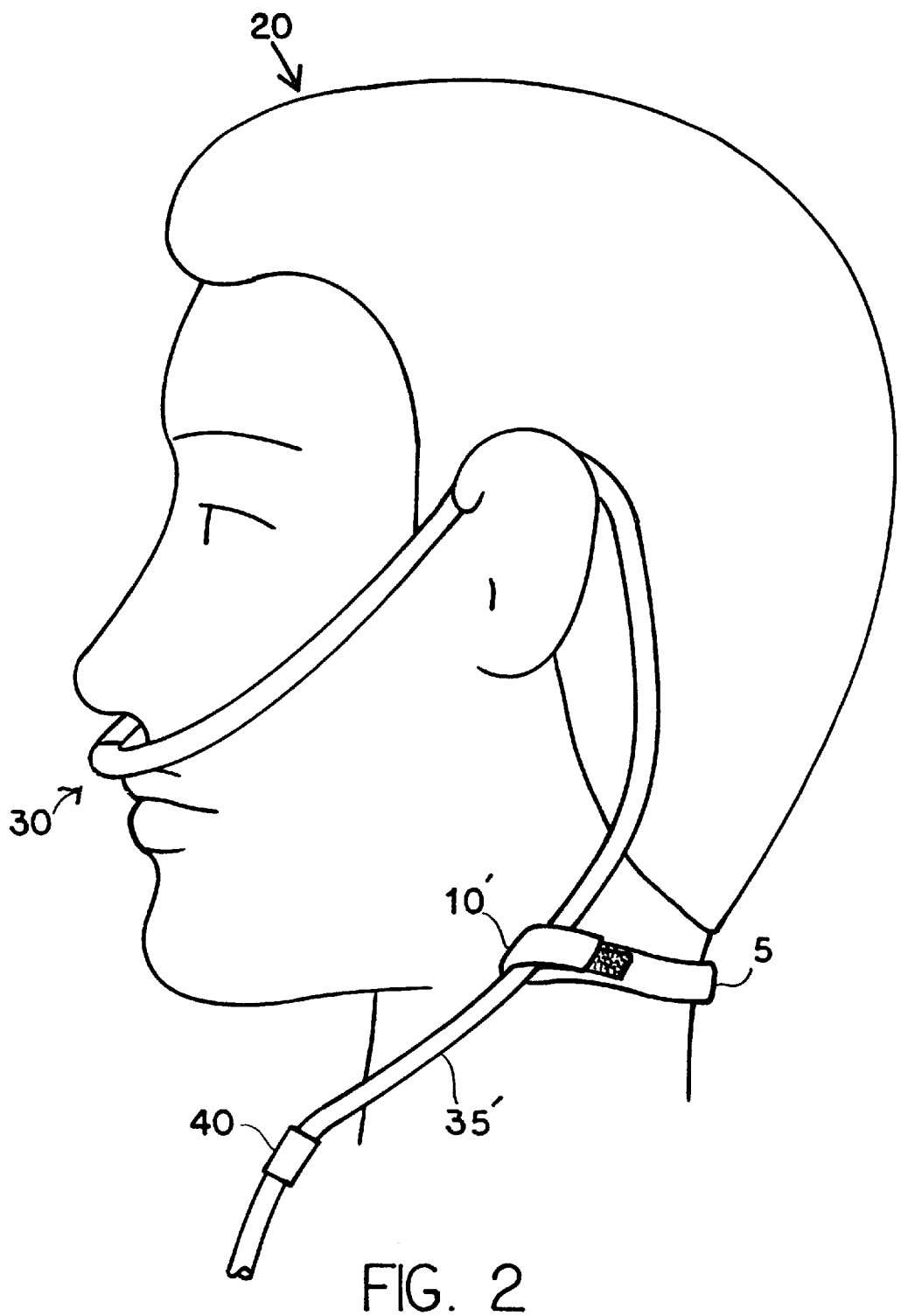
FIG. 2 is a left side view of a user wearing an embodiment of the invention.

In left side view FIG. 2, strap 5 and left side strap loop 10' of the invention may be seen beneath the left ear and behind the head, respectively, of the wearer 20. Cannula 30 with left tube 35' and clip 40 also appear in this Figure. In FIG. 2, strap 5 and left side strap loop 10' are worn on a lower position on the head than in FIG. 1.

Figure 3:
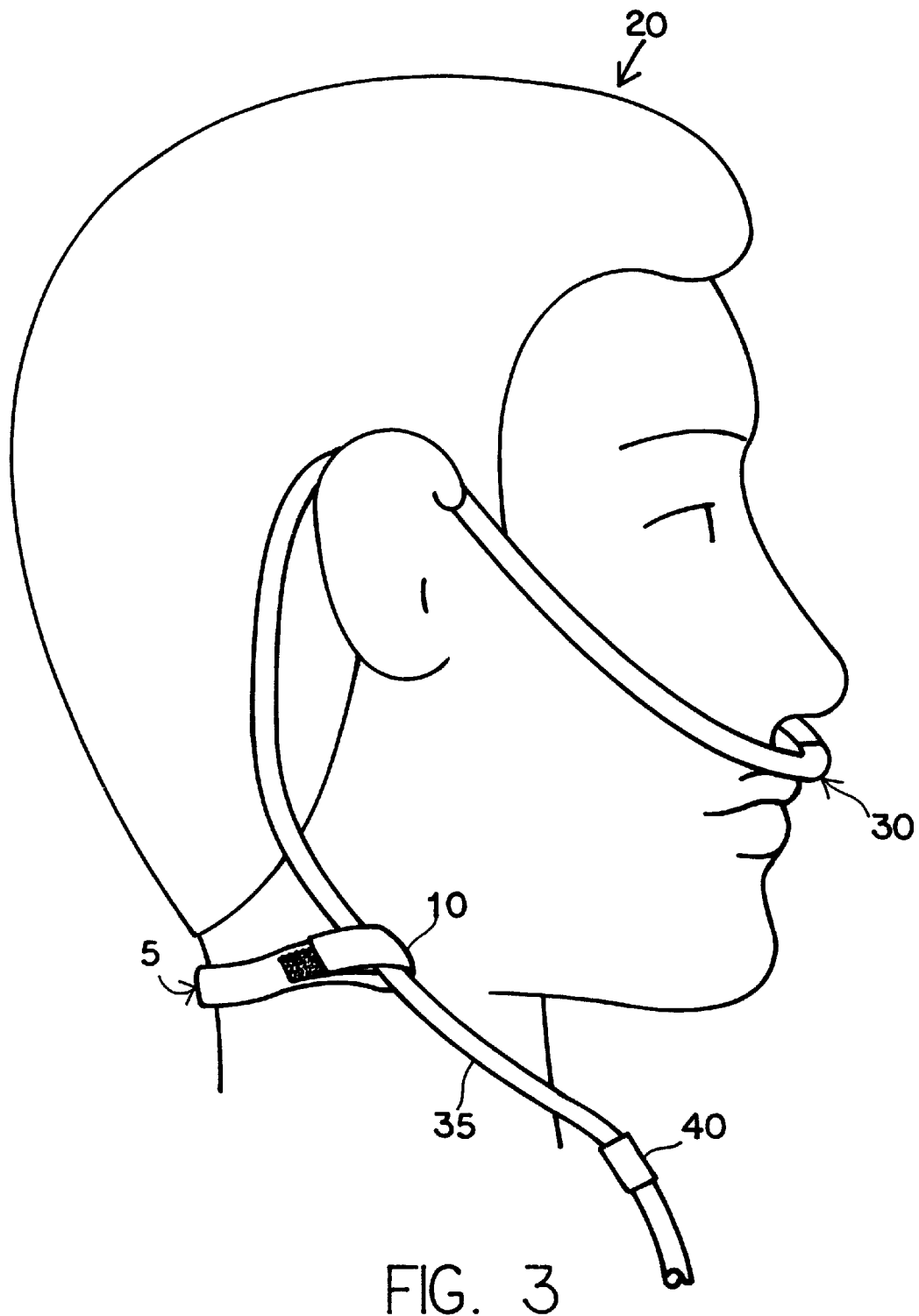
FIG. 3 is a right side view of a user wearing an embodiment of the invention.

In right side view FIG. 3, strap 5 and right side strap loop 10 of the invention may be seen beneath the right ear and behind the head, respectively, of the wearer 20. Cannula 30 with right tube 35 and clip 40 also appear in this Figure. In FIG. 3, strap 5 and right side strap loop 10 are worn at the same location as in FIG. 2.

Figure 4:
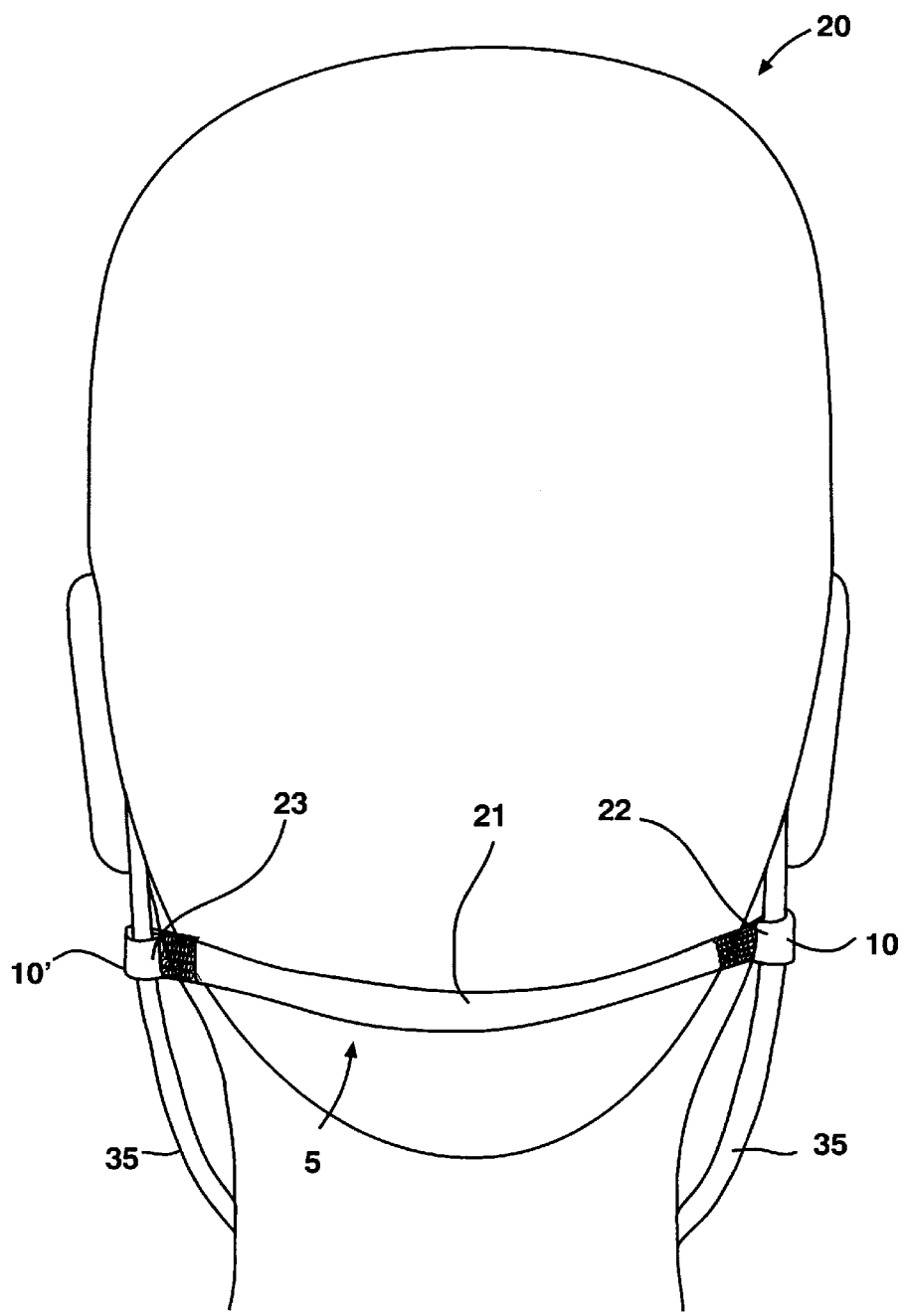
FIG. 4 is a back view of a user wearing an embodiment of the invention.

In back view FIG. 4, strap 5, left strap loop 10' and right side loop 10 of the invention may be seen beneath the ears and behind the head of wearer 20. Cannula left tube 35' and right tube 35 also appear in this Figure. In FIG. 4, strap 5 is worn at the same location as in FIG. 1.

In schematic view FIG. 5, strap 5 is depicted with width 18 (about 1/8–1/4 inch) and length 19 (about 6–16 inches). Strap 5 is preferably a single, elongated, one-piece strap, without apertures and without loops other than the distal end loops 10, 10'. The strap is preferably made of soft cloth or foam material, so that it does not necessarily require additional pads or cushions to be added to the strap for touching the patient's skin.

Outside surface 11 of the strap 5 has center 21 and distal ends 22, 23, each of which distal ends 22, 23 may be said to comprise a "distal area" at the outermost end of the strap and an "inner area" slightly closer to the center 21. The strap 56 has abutting strips of both hook section 12 and loop section 13 fasteners at each of the distal ends 22, 23. Typically, hook section 12 is at the "distal area" of each distal end 22, 23 of surface 11, and is shorter (about 1/5–1/3 times) than the length of loop section 13, which is located at the more proximal "inner area" of the ends 22, 23. Typically, hook section 12 is about 1/8–1/2 inch long, and loop section 13 is about 1/2–2 inches long. Typically, strap 5 and hook and loop sections 12 and 13, respectively, are all approximately the same width.

The preferred configuration of hook and loop fasteners may therefore be described as being all on a single surface of the invented strap, with no hook and loop fasteners, or fasteners of any kind, on the other surfaces of the strap. The hook section is adjacent to the loop section without any significant gap in between, so that the hook and loop material is substantially continuous along up to about 3 inches along each end of the strap. In this way, each loop 10, 10' around its respective cannula tube has an interior surface surrounding the cannula tube that is covered substantially entirely with hook and loop fastener. This positioning of the hook and loop fasteners and the inherent frictional nature of the hook and loop fasteners allows a significant range of adjustment of the tightness of the connection between the loops 10, 10' and the cannula tubes. For example, if a non-restrictive connection is desired, the loops 10, 10' may be made to be generally loose on the cannula tubes, or, if a more restrictive connection is desired, the loops 10, 10' may be tightened around the tubes. In this latter, restrictive connection, the small diameter of the loop and the frictional surface of the hook and/or loop fastener material contribute to the restrictive nature of the connection. Thus, it is not necessary or desired to provide a glued, taped, or other integral attachment of the strap 5 to the cannula tubes.

The above-described configuration of hook and loop fasteners allows securement of the cannula without complex structure. The invented system is a single, generally horizontal strap 5 that extends from cannula tube to cannula tube. There is no need for buckle mechanisms, and no need for the strap ends 22, 23 to meet or overlap. There is no need for any of the strap structure to extend forward across the patient's cheeks, lips, nose, or forehead. In its typical use, the forward-most portion of the invented strap, also the upward-most portion of the strap, is the loop 10, 10' around the cannula tubes.

In schematic partial view FIG. 6 including FIGS. 6A and 6B, outside surface 11, and inside surface 16 of substrate 17 are seen. The long section 13 of loop material shall preferably be made long enough to accommodate a variety of patient profile dimensions. The combination of both right and left side adjustments will allow an overall adjustment range equal to the length of the longer section 13. The width 18 is sufficient to allow adequate distribution of any pressure or tension developed by attachment of the support strap 5 to the left 35' and right 35 descending tubes of the nasal cannula 30. The length 19 shall be variable depending upon the application of the strap 5 to either adults, children, or infants.

The loop (10, 10') formed by folding the short hook section 12 back on the longer loop section 13, thereby enclosing the descending tube (35, 35') and maintaining said tube's relative position in front of and to the side of the neck of the patient does not necessarily create a restrictive connection to the said descending tube. If desired, a non-restrictive connection allows moderate movement of the descending tubes through the thereby created loops and minimizes unintended pulling on the nasal cannula caused by unconscious and/or involuntary movements of the sleeping patient.

Although this invention has been described above with reference to particular means, materials and embodiments, it is to be understood that the invention is not limited to these disclosed particulars, but extends instead to all equivalents within the scope of the following claims.

I claim:

1. A cannula securement system consisting only of an air delivery system and a single elongated cannula strap;

the air delivery system having a front, a rear, a top and a bottom, and consisting of:
 a nosepiece at the front of the air delivery system for extending into a user's nostrils and for being in fluid communication with the user's nostrils; and
 a hollow left cannula tube and a hollow right cannula tube extending rearward from the nosepiece and curving downward to form a left loop and a right loop at the rear of the air delivery system for draping over a user's left ear and for draping over a user's right ear, respectively, and the hollow left cannula tube and hollow right cannula tube further extending forward from the left loop and right loop for extending over the user's left and right shoulders, respectively, and coming together at a location below the nosepiece for crossing forward over a user's shoulders to the user's chest, wherein the hollow left cannula tube and hollow right cannula tube are in fluid communication with the nosepiece and are supplied with an oxygen-rich gas to provide oxygen-rich gas to the nosepiece; and
wherein the single elongated cannula strap has a center area and two distal ends;
wherein said two distal ends are attached to lower regions of said left loop and a lower region of said right loop;
wherein said cannula strap extends rearward from said lower regions of the left loop and said right loop with the two distal ends being the upward-most portion of the cannula strap;
wherein the single cannula strap comprises an adjustable fastener adapted to shorten, and thereby tension, the cannula strap, so that the cannula strap pulls the left loop and right loop rearward and does not lift the left loop and right loop upwards.

2. The system as in claim 1, wherein said strap is flat, and has a first surface, and a second surface, wherein said adjustable fastener of each distal end comprises a hook patch and a loop patch of hook and loop fastener on the first surface, and wherein the second surface has no hook patches and no loop patches.

3. The system as in claim 2, wherein the hook patches and the loop patches are closely adjacent to each other with no space in between.

* * * * *